United States Patent [19]
Takeuchi et al.

[11] Patent Number: 5,972,198
[45] Date of Patent: Oct. 26, 1999

[54] CORROSION RESISTANCE TEST PROCESS FOR ARTICLE FORMED OF METAL MATERIAL AND COATING

[75] Inventors: Toshihiro Takeuchi; Tadashi Imanaka, both of Wako; Keiji Kiuchi, Kiryu; Hidemichi Ohta, Kiryu, all of Japan

[73] Assignees: Mitsuba Corporation, Gunma; Honda Giken Kogyo Kabushiki Kaisha, Tokyo, both of Japan

[21] Appl. No.: 09/071,915

[22] Filed: May 5, 1998

[30] Foreign Application Priority Data

May 6, 1997 [JP] Japan ................................ 9-115840

[51] Int. Cl.[6] .................................................. G01N 27/26
[52] U.S. Cl. ..................... 205/776.5; 205/775.5; 205/341; 205/342; 324/71.2; 324/700; 324/713
[58] Field of Search ............................. 205/775.5, 776.5, 205/728, 341, 342, 85, 106, 107, 220, 223; 204/404, 434; 324/71.1, 71.2, 700, 713

[56] References Cited

U.S. PATENT DOCUMENTS

| | | | |
|---|---|---|---|
| 4,266,187 | 5/1981 | Slough | 324/71.2 |
| 5,338,417 | 8/1994 | Brücken et al. | 205/728 |
| 5,466,349 | 11/1995 | Tench et al. | 205/776.5 |
| 5,519,330 | 5/1996 | Yamauchi et al. | 324/700 |
| 5,529,683 | 6/1996 | Critz et al. | 205/342 |

FOREIGN PATENT DOCUMENTS 7-195612 8/1995 Japan.
WO97/47961 12/1997 WIPO.

OTHER PUBLICATIONS

Patent Abstracts of Japan, JP-4 076447, Mar. 11, 1992.

*Primary Examiner*—Bruce F. Bell
*Attorney, Agent, or Firm*—Nikaido, Marmelstein, Murray & Oram LLP

[57] ABSTRACT

It is an object of the present invention to provide a corrosion resistance test process, wherein the estimation of the corrosion resistance of an article formed of a metal material and a coating can be carried out synthetically and in a short time. In carrying out a corrosion resistance test, the article is immersed into an electrolytic solution and then, a voltage is applied to the metal material to carry out a metal material corroding step and a coating peeling-off step alternatively and repeatedly. The voltage applied to the metal material is a superimposed voltage Vd+Va resulting from superimposition of a DC voltage Vd and an AC voltage Va. A voltage condition of Vd<0 and Vd+Va>0 is established at the metal material corroding step, while a voltage condition of Vd<0 and Vd+Va<0 is established at the coating peeling-off step.

5 Claims, 6 Drawing Sheets

CORROSION RESISTANCE TEST PROCESS FOR ARTICLE FORMED OF METAL MATERIAL AND COATING

BACKGROUND OF THE INVENTION

1. Field of the Invention

The present invention relates to a corrosion resistance test process for an article formed of a metal material and a coating formed on the metal material.

2. Description of Related Art

A cathode peeling-off test process is conventionally known as a test process for examining the adhesion force of a coating in an article of the above-described type (for example, see Japanese Patent Application Laid-open No.7-195612). In this test process, a procedure is employed which comprises the steps of immersing an article having a damaged portion reaching the metal material into an aqueous solution of NaCl as an electrolytic solution and then allowing a DC current to flow between the metal material having a negative polarity and an electrode placed in the aqueous solution of NaCl.

During supplying of the current, in the metal material having a negative polarity a nascent OH ion produced by the electrolysis of water reduces the force of adhesion of the coating to the metal material, starting from the damaged portion of the coating, and an $H_2$ gas simultaneously generated peels off the coating by a physical action thereof.

In this way, the cathode peeling-off test process has an advantage that the relative excellence of the adhesion force of the coating can be determined simply, but the corrosion of the metal material attendant on the peeling-off of the coating cannot be predicted. Therefore, the cathode peeling-off test process suffers from a problem that the synthetic estimation of corrosion resistance cannot be performed for the article.

Therefore, a cycle corrosion test (CCT) has been employed which is capable of estimating both the peeling-off of the coating and the corrosion (the anode oxidation) of the metal material. This cycle corrosion test (CCT) suffers from a problem that test results cannot be obtained quickly, because a lot of test time is required to complete the test.

SUMMARY OF THE INVENTION

It is an object of the present invention to provide a corrosion resistance test process of the above-described type, wherein both the peeling-off of the coating and corrosion of the metal material can be estimated by employing a relatively simple means, and the test time can be shortened considerably.

To achieve the above object, according to the present invention, there is provided a corrosion resistance test process for an article, comprising the steps of immersing an article formed of a metal material and a coating formed on the metal material into an electrolytic solution (a wide range of which are well known to those skilled in the art), and then applying a voltage to said metal material to carry out a metal material corroding step and a coating peeling-off step alternately and repeatedly (i.e., the metal material corroding step and the coating peeling-off step are conducted alternately, each of the two steps being carried out plural times), the voltage applied to the metal material being a superimposed voltage Vd+Va resulting from the superimposition of a DC voltage Vd and an AC voltage Va; a voltage condition of Vd<0 and Vd+Va>0 being established at the metal material corroding step, while a voltage condition of Vd<0 and Vd+Va<0 being established at the coating peeling-off step.

If a measure of the above-described type is employed, the peeling-off of the coating and the corrosion of the metal material, starting from the damaged portion, are carried out alternately repeatedly by the instantaneous polarity change of the superimposed voltage Vd+Va. Thus, the surface passivation for bringing the metal material surface into an active state simultaneously with the promotion of the peeling-off of the coating can be prevented to allow the corrosion to advance sufficiently. Therefore, the synthetic estimation of the corrosion resistance can be performed in a short time. In addition, a concave surface produced due to the corrosion of the metal material is a concave arcuate surface, whereby the corrosion closely allied to the corrosion in the natural world can be reproduced. The damaged portion of the coating includes a thin portion, pinhole or the like in addition to a peeled-off portion.

The invention may be more fully understood with reference to the accompanying drawings and the following description of the embodiments shown in those drawings. The invention is not limited to the exemplary embodiments and should be recognized as contemplating all modifications within the skill of an ordinary artisan.

BRIEF DESCRIPTION OF THE DRAWING FIGURES

DETAILED DESCRIPTION OF PREFERRED EMBODIMENTS

Figure 1:
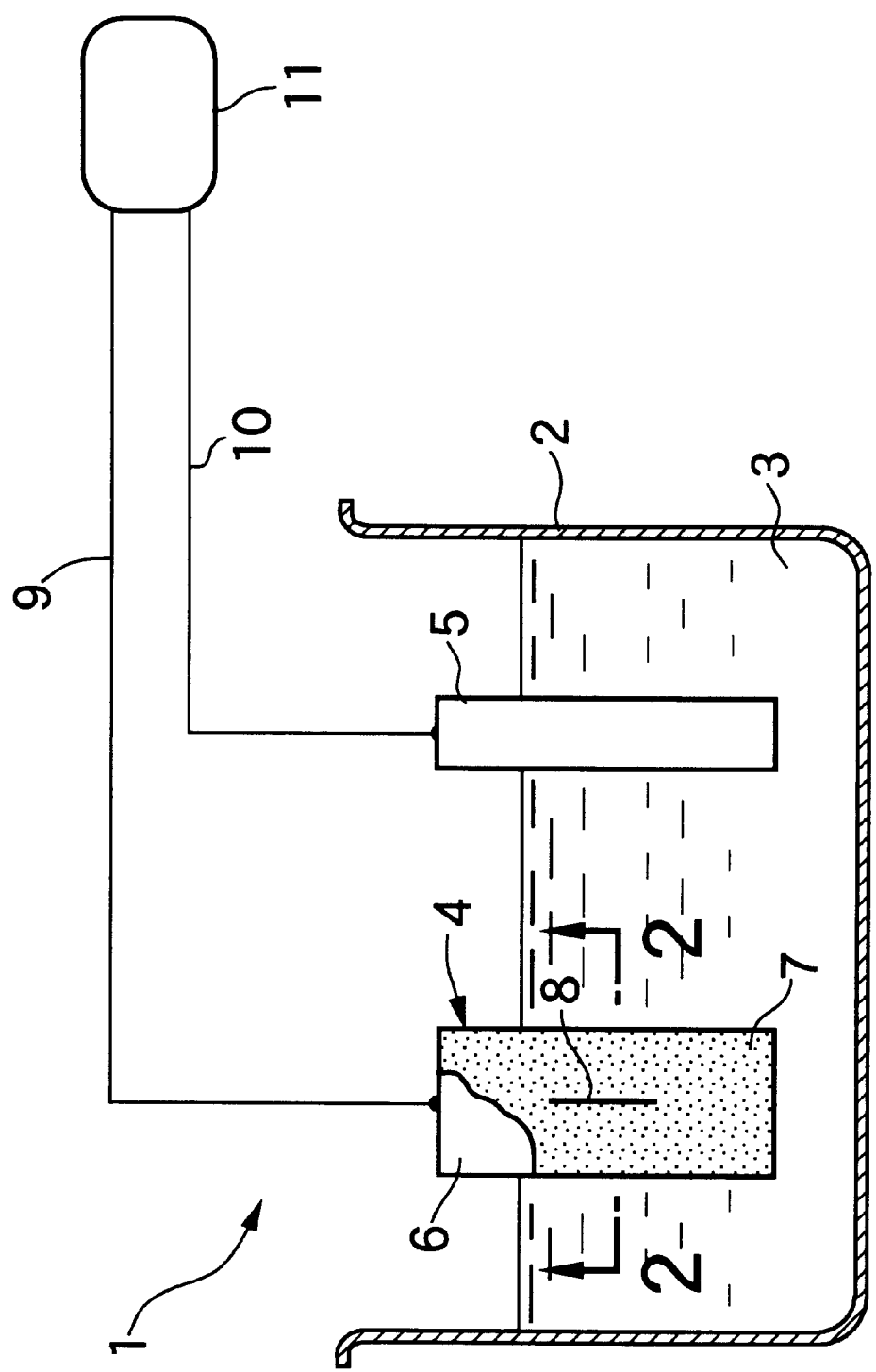
FIG. 1 is a schematic view of experiment equipment for a corrosion resistance test apparatus.
Figure 2:
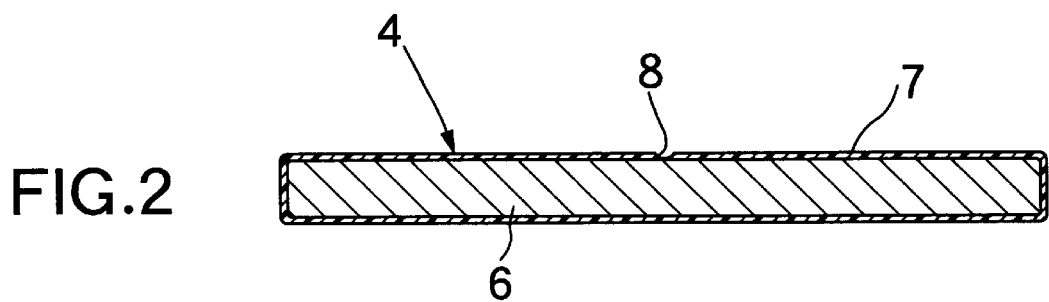
FIG. 2 is an enlarged sectional view taken along the line II—II in FIG. 1.

FIG. 1 shows experiment equipment 1 for a corrosion resistance test apparatus. An aqueous solution 3 of NaCl as an electrolytic solution is stored in an electrolytic bath 2. A plate-shaped article 4 and a plate-shaped electrode 5 are immersed into the aqueous solution 3 of NaCl. The article 4 is comprised of a steel plate 6 as a metal material and a coating 7 formed on the entire steel plate 6. As best shown in FIG. 2, a damaged portion 8 reaching the steel plate 6 is formed in the coating 7 by a cutter. The electrode 5 is formed from carbon. The steel plate 6 and the electrode 5 are connected to a power source 11 through current supply passages 9 and 10. The power source 11 is formed to be able to apply a superimposed voltage Vd+Va resulting from superimposition of a DC voltage Vd and an AC voltage Va to the steel plate 6 (wherein |Va|>|Vd |).

Figure 3:
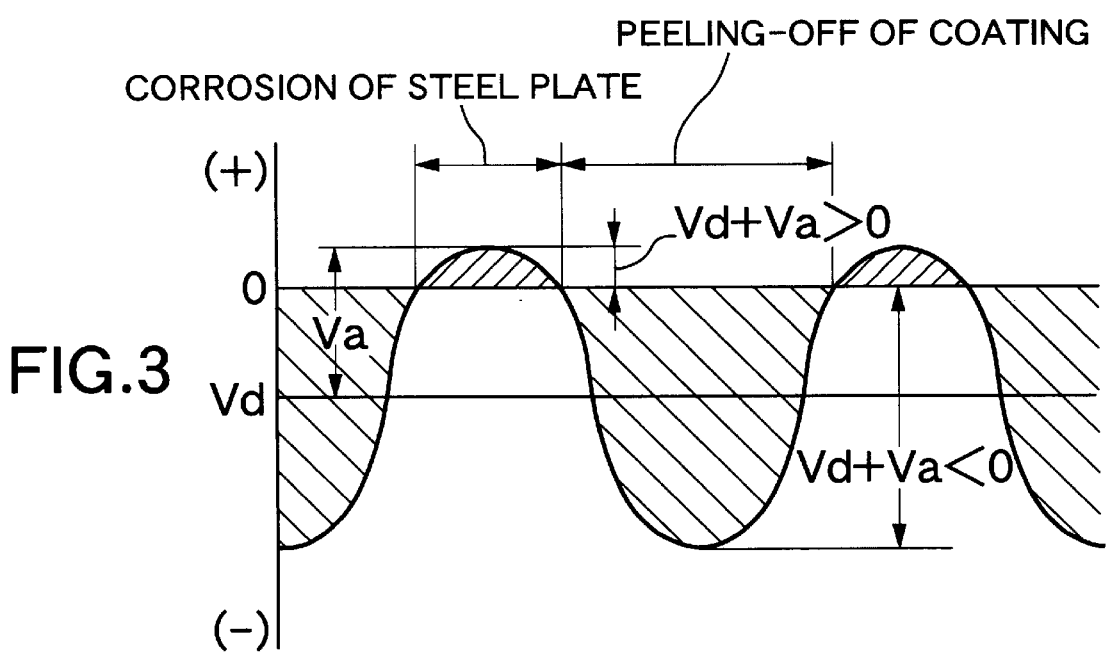
FIG. 3 is a wave form diagram of a superimposed voltage Vd+Va.

FIG. 3 shows the wave form of the superimposed voltage Vd+Va applied to the steel plate 6. At a steel plate corroding step, a voltage condition of Vd<0 and Vd+Va>0 is established in the steel plate 6. Thus, the polarity of the steel plate 6 is maintained positive and hence, an anode oxidation phenomenon is generated in the steel plate 6. On the other hand, at a coating peeling-off step, a voltage condition of Vd<0 and Vd+Va<0 is established in the steel plate 6. Thus, the polarity of the steel plate 6 is maintained negative, and hence, the peeling-off of the coating by nascent OH ion and $H_2$ gas is carried out as described above. In the corrosion resistance test, both of the steps are alternately and repeatedly carried out over a predetermined time.

In this case, if the time for which the polarity of the steel plate 6 is maintained positive and the time for which the polarity of the steel plate 6 is maintained negative are compared, the latter is sufficiently longer than the former. The corrosion of the steel plate 6 reliably advances even if the positive maintaining time is short and hence, any problem is not produced. For the peeling-off of the coating 7, it is necessary to sufficiently generate the OH ion and the $H_2$ gas. Therefore, if the negative maintaining time is too short, the peeling-off of the coating 7 does not advance satisfactorily. So long as the negative maintaining time is sufficient, the above-described problem does not arise.

If the DC voltage Vd applied to the steel plate 6 is larger than 0 (zero) at either of the steps, the corrosion of the steel plate 6 is excessively large, on the one hand, and the peeling-off of the coating 7 is excessively small, on the other hand, and hence, it is difficult to justly estimate the corrosion resistance of the article 4.

EXAMPLE 1

A steel plate 6 having a width of 70 mm, a length of 150 mm and a thickness of 1 mm was subjected to a pretreatment using a pretreating agent (made under a trade name of SD2800 by Nippon Paint, Co.). Then, the entire steel plate 6 was subjected to a cation electro-deposition coating step to form a coating 7 having thickness of 20 to 25 μm, thereby providing an article 4. Thereafter, a damaged portion 8 having a length of 50 mm was formed in the coating 7 using a cutter.

Using this article 4, the corrosion resistance test was carried out under the following conditions: the concentration of the aqueous solution of NaCl was 3%; the temperature of the aqueous solution of NaCl was 45° C.; the DC voltage Vd applied to the steel plate 6 was equal to –6 V (constant); the AC voltage Va was equal to 12, 17 or 30 V; and the frequency of the voltage was 50 Hz.

Figure 4:
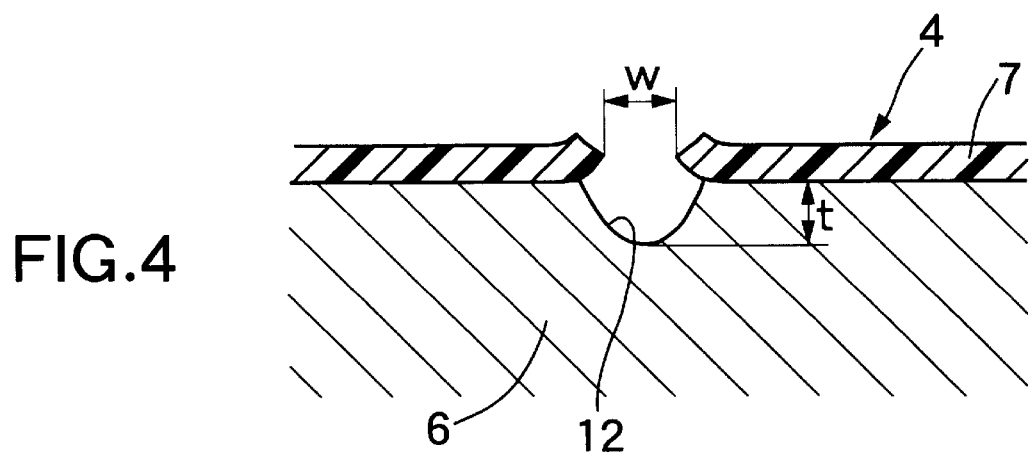
FIG. 4 is an enlarged sectional view of an essential portion of an article showing the peeling-off of a coating and the corrosion of a steel plate.

In this corrosion resistance test, as shown in FIG. 4, the peeling-off of the coating 7 and the corrosion of the steel plate 6 started from the damaged portion 8 occurred. The inner surface of a recessed portion 12a formed due to such corrosion was a concave arcuate surface. Therefore, when the relationship between the test time and the peeled-off width w of the coating 7 as well as the amount t of decrement in plate thickness was examined, results shown in FIGS. 5 and 6 were obtained.

Figure 5:
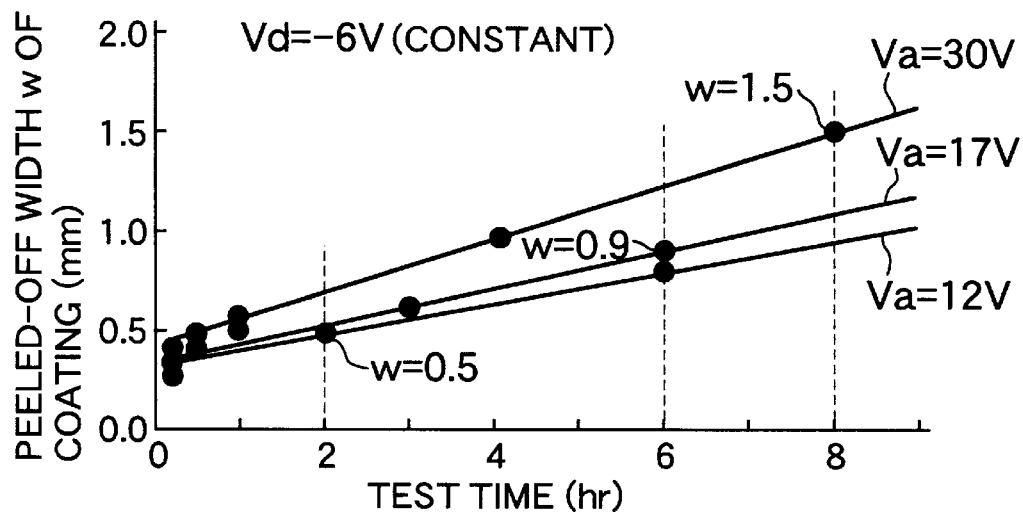
FIG. 5 is a graph showing one example of the relationship between the test time and the peeled-off width w of the coating.

It can be seen from FIG. 5 that the peeled-off width w of the coating 7 increased substantially proportionally with respect to the passage of the test time. It is also apparent that if the AC voltage Va is increased, the peeled-off width w per unit time is increased.

Figure 6:
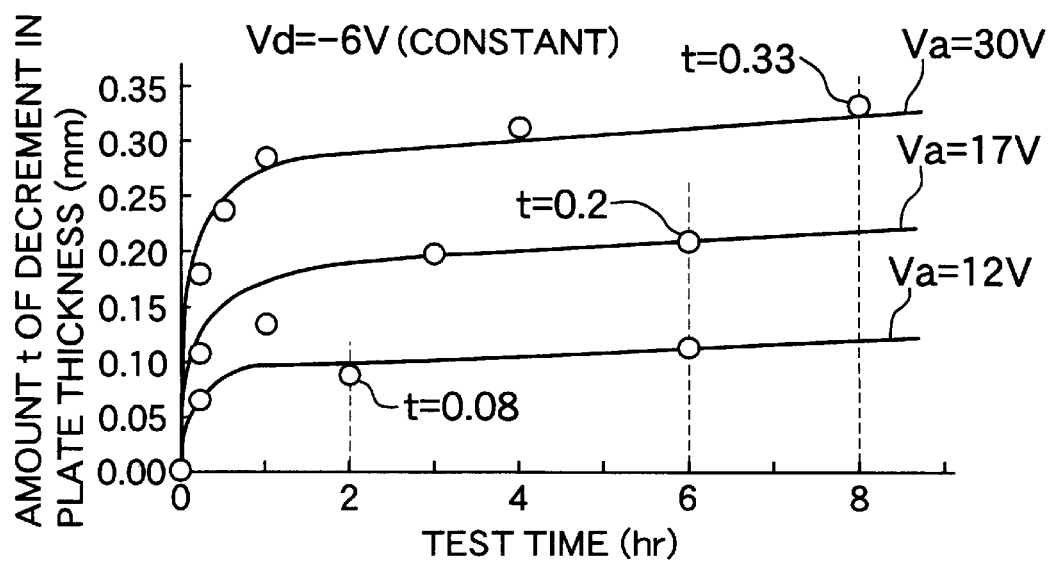
FIG. 6 is a graph showing one example of the relationship between the test time and the amount t of decrement in plate thickness.

On the other hand, it can be seen from FIG. 6 that the amount t of decrement in plate thickness is steeply increased in a relatively short time, but thereafter, the degree of increase in the amount t becomes extremely gentle. This is because, if a new exposed surface appears in the steel plate 6 with the advance of the peeling-off of the coating 7, the corrosion of such exposed surface advances preferentially, and in accordance with this, the advance of the corrosion in a thickness-wise direction becomes slow. It is also apparent that if the AC voltage Va is increased, the amount t of decrement in plate thickness per unit time is increased.

Figure 7:
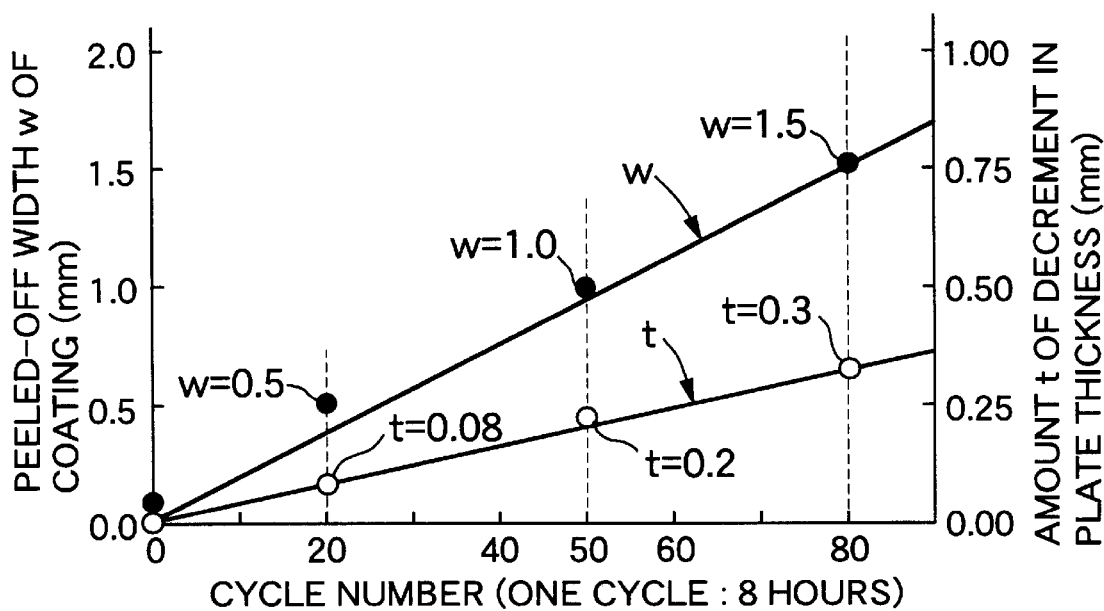
FIG. 7 is a graph showing the relationship between the cycle number and the peeled-off width w of the coating as well as the amount t of decrement in plate thickness.

FIG. 7 shows results of a cycle corrosion test process (CCT) using the article 4 similar to that described above. Test conditions required to provide test results substantially equivalent to test results of the composite corrosion test process at 20, 50 and 80 cycles (one cycle of 8 hours) were found in FIGS. 5 and 6, thereby providing results shown in Table 1.

TABLE 1

| Cycle corrosion test process | | | | |
|---|---|---|---|---|
| | | | Example | |
| Cycle number (one cycle of 8 hours) | Peeled off width w of coating (mm) | Amount t of decrement in plate thickness (mm) | AC voltage Va (V) | Test time (hr) |
| 20 (160 hr) | 0.5 | 0.08 | 12 | 2 |
| 50 (400 hr) | 1.0 | 0.2 | 17 | 6 |
| 80 (640 hr) | 1.5 | 0.3 | 30 | 8 |

As is apparent from Table 1, according to the example, the corrosion resistance of the article 4 can be justly estimated in an extremely short test time, as compared with the cycle corrosion test process.

Then, a corrosion resistance test was carried out using the article 4 having the damaged portion 8, similar to that described above, while changing the AC frequency so as to become higher than 50 Hz, under the following conditions: the concentration of the aqueous solution of NaCl was 3%; the temperature of the aqueous solution was 45° C.; the DC voltage Vd applied to the steel plate 6 was equal to –10 V (constant); the AC voltage Va was equal to 14 V (constant); and the test time was one hour.

Figure 8:
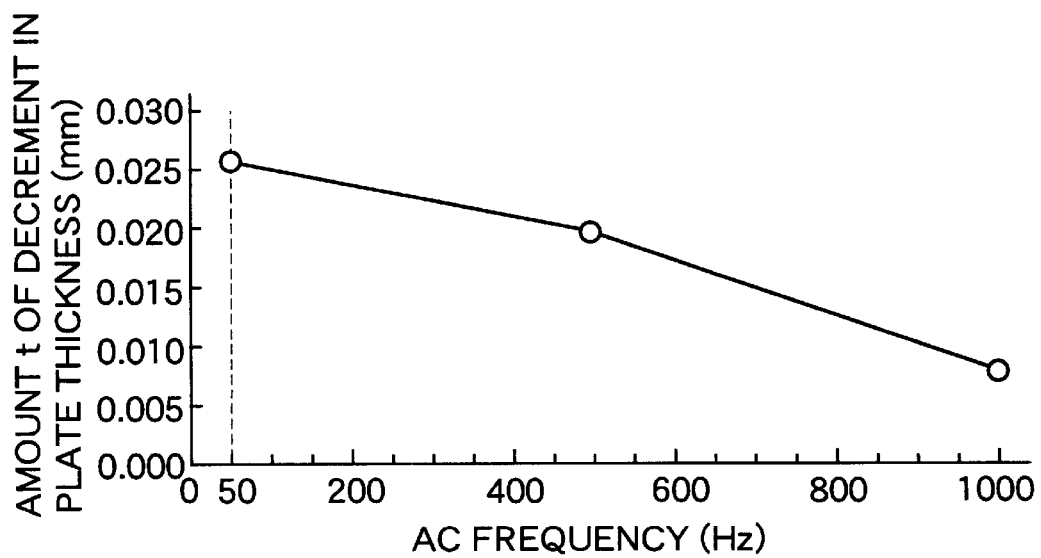
FIG. 8 is a graph showing the relationship between the AC frequency and the amount t of decrement in plate thickness.

FIG. 8 shows the relationship between the AC frequency and the amount t of decrement in plate thickness in the corrosion resistance test. It can be seen from FIG. 8 that the amount t of decrement in plate thickness is reduced, as the AC frequency becomes higher than 50 Hz. On the other hand, if it is considered that the efficiency of output from the power source is degraded if the AC frequency is smaller than 50 Hz, the AC frequency is suitable to be 50 Hz.

EXAMPLE 2

A corrosion resistance test was carried out using an article 4 having a damaged portion 8, similar to that used in Example 1, under the following conditions: the concentration of the aqueous solution of NaCl was 3%; the temperature of the aqueous solution of NaCl was 45° C.: the AC voltage Va was equal to 30 V (constant); the frequency of the AC voltage was 50 Hz; and the DC voltage Vd applied to the steel plate 6 was equal to –6, –8 or –10 V.

Figure 9:
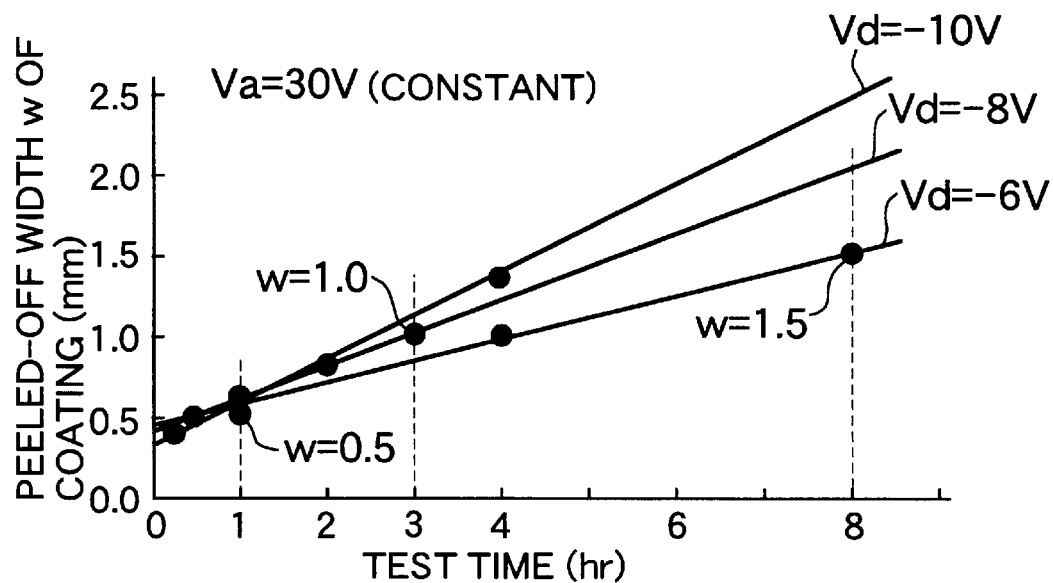
FIG. 9 is a graph showing another example of the relationship between the test time and the peeled-off width w of the coating.
Figure 10:
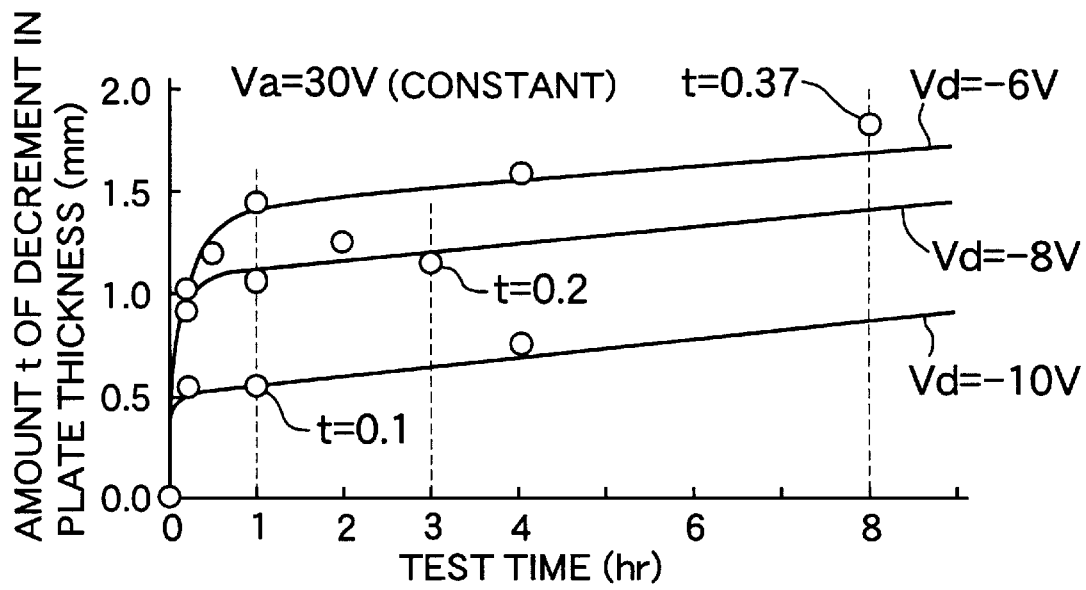
FIG. 10 is a graph showing another example of the relationship between the test time and the amount t of decrement in plate thickness.

The relationship between the test time and the peeled-off width w of the coating 7 as well as the amount t of decrement in plate thickness in this corrosion test was examined, thereby providing results shown in FIGS. 9 and 10.

It can be seen from FIG. 9 that the peeled-off width w of the coating 7 is increased substantially proportionally with respect to the passage of the test time. It is also apparent that if the DC voltage Vd is dropped from −6 V to −8 V or −10 V, the peeled-off width w per unit time is increased. This is because, if the DC voltage Vd is dropped at the constant AC voltage Va, the time for which the polarity of the steel plate 6 is maintained negative is prolonged in accordance with such dropping.

On the other hand, it can be seen from FIG. 10 that the amount t of decrement in plate thickness is steeply increased in a relatively short time, but thereafter, the increase in the amount t of decrement becomes extremely gently. If the DC voltage Vd is increased from −10 V to −8 V or −6 V, the amount t of decrement per unit time is increased. This is because, if the DC voltage Vd is increased at a constant AC voltage Va, the time for which the polarity of the steel plate 6 is maintained positive is prolonged in accordance with such rising.

As in Example 1, conditions required to provide test results substantially equivalent to those of the cycle corrosion test process (CCT) at 20, 50, and 80 (one cycle of 8 hours) were found in FIGS. 9 and 10, thereby providing results shown in Table 2.

TABLE 2

| Cycle corrosion test process | | | | |
|---|---|---|---|---|
| | | Amount t of | Example | |
| Cycle number (one cycle of 8 hours) | Peeled off width w of coating (mm) | decrement in plate thickness (mm) | DC voltage Va (V) | Test time (hr) |
| 20 (160 hr) | 0.5 | 0.08 | −10 | 1 |
| 50 (400 hr) | 1.0 | 0.2 | −8 | 3 |
| 80 (640 hr) | 1.5 | 0.3 | −6 | 8 |

As is apparent from Table 2, according to the example, the corrosion resistance of the article 4 can be justly estimated in an extremely short test time, as compared with the cycle corrosion test process.

COMPARATIVE EXAMPLE

A corrosion resistance test was carried out using an article 4 having a damage portion 8, similar to that used in Example 1, under the following conditions: the concentration of the aqueous solution of NaCl was 3%; the temperature of the aqueous solution of NaCl was 45° C.; the AC voltage Va was equal to 8 V; and the frequency of the AC voltage Va was 50 Hz, namely, with only the AC voltage being used.

Figure 11:
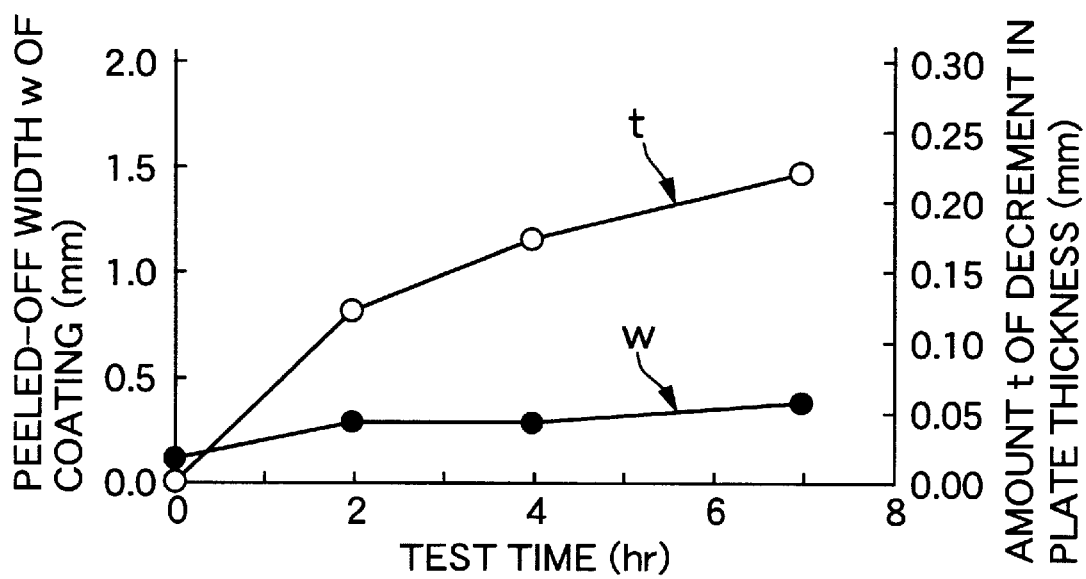
FIG. 11 is a graph showing the relationship between the test time and the peeled-off width w of the coating as well as the amount t of decrement in plate thickness.

The relationship between the test time and the peeled-off width w of the coating 7 as well as the amount t of decrement in plate thickness in this corrosion resistance test was examined, thereby providing results shown in FIG. 11.

When the supply of AC current was carried out, the time for which the polarity of the steel plate 6 is maintained positive and the time for which the polarity of the steel plate 6 is maintained negative are theoretically equal to each other. Therefore, the amount of iron (Fe) eluted in the steel plate 6 and the amount of iron (Fe) precipitated are equal to each other and hence, the thickness of the steel plate 6 is not decreased.

Actually, however, the Fe elution reaction is preferable to the Fe precipitation reaction by such a reason that the AC wave form is not a correct sine wave, and as a result, the thickness of the steel plate 6 is decreased, as shown by a line t in FIG. 11. On the other hand, in the case of the supply of the AC current, the time for which the polarity of the steel plate 6 is maintained negative is extremely short and hence, the amount of nascent OH ion produced is insufficient. As a result, the peeling-off of the coating 7 little advances, as shown by a line w in FIG. 11.

According to the present invention, it is possible to provide a corrosion resistance test process, wherein the peeling-off of the coating and the corrosion of the metal material, starting from the damaged portion of the coating such as a thinned portion, pinhole or the like, can be sufficiently promoted by employing the above-described measure to shorten the test time considerably, whereby the synthetic estimation of the corrosion resistance can be carried out for the article in a short time.

Although the corrosion resistance test process in accordance with the present invention have been described in connection with preferred embodiments, it will be appreciated by those skilled in the art that modifications not specifically described may be made without departing from the spirit and scope of the invention defined in the following claims.

We claim:

1. A corrosion resistance test process for an article comprising the steps of immersing an article formed of a metal material and a coating formed on the metal material into an electrolytic solution, and then applying a voltage to said metal material to carry out (1) a metal material corroding step and (2) a coating peeling-off step alternately and repeatedly, said voltage applied to said metal material being a superimposed voltage Vd+Va resulting from the superimposition of a DC voltage Vd and an AC voltage Va; a voltage condition of Vd<0 and Vd+Va>0 being established during said metal material corroding step, and a voltage condition of Vd<0 and Vd+Va <0 being established during said coating peeling-off step.

2. A corrosion resistance test process for an article according to claim 1, wherein when said DC voltage Vd is constant, said AC voltage Va is increased in proportion to elapsed time.

3. A corrosion resistance test process for an article according to claim 1, wherein when said AC voltage Va is constant, said DC voltage Vd is increased in proportion to elapsed time.

4. A corrosion resistance test process for an article according to claim 1, wherein said AC voltage Va is in the range of from 12 V to 30 V.

5. A corrosion resistance test process for an article according to claim 1, wherein DC voltage is in the range of from −6 V to −10 V.

* * * * *